(12) United States Patent
Van Nijnatten

(10) Patent No.: US 10,820,872 B2
(45) Date of Patent: Nov. 3, 2020

(54) X-RAY CONTROLLED CONTRAST AGENT INJECTION

(71) Applicant: KONINKLIJKE PHILIPS N.V., Eindhoven (NL)

(72) Inventor: Fred Simon Berend Van Nijnatten, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 283 days.

(21) Appl. No.: 14/650,055

(22) PCT Filed: Dec. 13, 2013

(86) PCT No.: PCT/IB2013/060927
§ 371 (c)(1),
(2) Date: Jun. 5, 2015

(87) PCT Pub. No.: WO2014/097094
PCT Pub. Date: Jun. 26, 2014

(65) Prior Publication Data
US 2016/0278725 A1 Sep. 29, 2016

(30) Foreign Application Priority Data

Dec. 19, 2012 (EP) .................................. 12198103

(51) Int. Cl.
*A61B 5/11* (2006.01)
*A61B 6/00* (2006.01)
(Continued)

(52) U.S. Cl.
CPC ............ *A61B 6/481* (2013.01); *A61B 5/0275* (2013.01); *A61B 5/1128* (2013.01);
(Continued)

(58) Field of Classification Search
CPC ................................ A61B 6/481; A61B 6/504
See application file for complete search history.

(56) References Cited

U.S. PATENT DOCUMENTS 5,687,208 A * 11/1997 Bae ..................... G06F 19/3437
378/8
5,840,026 A * 11/1998 Uber, III .................. A61B 8/06
128/DIG. 12
(Continued)

FOREIGN PATENT DOCUMENTS

| JP | 2008161675 A | 7/2008 |
|----|--------------|--------|
| JP | 2009519082 A | 5/2009 |

(Continued)

OTHER PUBLICATIONS

Pereira, V.M. et al. "A DSA-Based Method Using Contrast-Motion Estimation for the Assessment of the Intra-Aneurysmal Flow Changes Induced by Flow-Diverter Stents", Am J. Neuroradiol, Nov. 2012.
(Continued)

*Primary Examiner* — Hien N Nguyen

(57) ABSTRACT

An imaging system including a closed-loop controller (FC) for automatically adapting a power injector system (PJ). The power injector (PJ) injects contrast agent into an object (V) and the imager (100) acquires one or more images (AN, AN i) of the object (V) with the contrast agent resident therein. The controller (FC) calculates a desired optimal injection rate from the images (AN, $AN_i$). Controller (FC) then controls the injector (PJ) according to the calculated optimal injection rate.

14 Claims, 6 Drawing Sheets

(51) Int. Cl.
*A61M 5/00* (2006.01)
*A61M 5/142* (2006.01)
*A61B 5/0275* (2006.01)

(52) U.S. Cl.
CPC ............ *A61B 6/4441* (2013.01); *A61B 6/461* (2013.01); *A61B 6/469* (2013.01); *A61B 6/486* (2013.01); *A61B 6/504* (2013.01); *A61B 6/54* (2013.01); *A61M 5/007* (2013.01); *A61B 6/467* (2013.01); *A61M 2005/14208* (2013.01)

(56) References Cited

U.S. PATENT DOCUMENTS

| | | | |
|---|---|---|---|
| 6,052,476 | A | 4/2000 | Qian et al. |
| 6,385,483 | B1 | 5/2002 | Uber et al. |
| 7,672,711 | B2 | 3/2010 | Haras et al. |
| 8,160,679 | B2 | 4/2012 | Uber et al. |
| 8,208,699 | B2 | 6/2012 | Hay et al. |
| 8,340,744 | B2 | 12/2012 | Bredno et al. |
| 9,597,447 | B2 | 3/2017 | Masuda et al. |
| 2002/0172323 | A1 | 11/2002 | Karellas et al. |
| 2004/0101090 | A1 | 5/2004 | Drummond et al. |
| 2005/0203389 | A1 | 9/2005 | Williams |
| 2007/0078338 | A1 | 4/2007 | Pedain et al. |
| 2009/0198121 | A1 | 8/2009 | Hoheisel |
| 2010/0002925 | A1 | 1/2010 | Kiraly et al. |
| 2010/0183206 | A1* | 7/2010 | Carlsen ............... A61B 6/032 382/128 |
| 2010/0292570 | A1 | 11/2010 | Tsukagoshi et al. |
| 2010/0305446 | A1 | 12/2010 | Berard-Anderson et al. |
| 2011/0066024 | A1 | 3/2011 | Shih et al. |
| 2013/0345548 | A1* | 12/2013 | Hynes ............... A61M 5/007 600/420 |
| 2014/0005533 | A1 | 1/2014 | Grasruck et al. |
| 2016/0278725 | A1 | 9/2016 | Van Nijnatten |

FOREIGN PATENT DOCUMENTS

| | | |
|---|---|---|
| JP | 2011235113 A | 11/2011 |
| WO | 9631156 A1 | 4/1996 |
| WO | 0064353 A2 | 11/2000 |
| WO | 2007069166 A2 | 6/2007 |

OTHER PUBLICATIONS

Shpilfoygel, S.D. et al., "X-ray videodensitometric methods for blood flow and velocity measurement: a critical review of literature", Med. Phys. 27, 2008-2023 (2000).

Bonnefous, O. et al., "Quantification of arterial flow using digital subtraction angiography," Med. Phys. 39 (10), Oct. 2012.

* cited by examiner

X-RAY CONTROLLED CONTRAST AGENT INJECTION

FIELD OF THE INVENTION

The present invention relates to an imaging system, to a method of controlling a power injector, to a computer program element and to a computer readable medium.

BACKGROUND OF THE INVENTION

Angiography is an imaging technique that is used to render visible, in projection images acquired by radiation based imaging equipment, structures that do not normally have the required radiation opacity. In order to at least temporarily confer radio opacity to those structures, a contrast agent is introduced into the relevant body fluid, e.g. blood, of a patient.

Angiographic techniques are not only used to assess vascular geometry but also to assess functional parameters such as flow and perfusion at a region of interest.

Understanding the flow characteristics is for example useful when checking the correct placement of a blood flow diverter (essentially a type of stent) in a vessel. To this end, after placement of the diverter at the lesioned site, a sequence of angiographic images are obtained thereof and then image-processed to evaluate the blood flow. It has been found however, that the accuracy and fidelity of the hemodynamic information obtained by such angiographic image analysis is not always satisfactory. Potentially dangerous hemodynamic behaviors may pass undetected and may prove fatal in the case of some aneurysms.

SUMMARY OF THE INVENTION

There may therefore be a need for an imaging system or method to improve the accuracy of hemodynamic parameter determination and/or related investigations concerning a fluid's dynamic behavior.

The object of the present invention is solved by the subject matter of the independent claims wherein further embodiments are further incorporated in the dependent claims. It should be noted that the following described aspects of the invention equally apply to the method of controlling a power injector, to the computer program element and to the computer readable medium.

According to a first aspect of the invention there is provided an imaging system that includes an imager and a controller for a power injector or similar device that drives a fluid flow. The controller comprises:
  an input port for receiving i) a current power injector setting and ii) a current one or more image of an object. The one or more image is acquired by the imager whilst a fluid is flowing or resides in an object's region of interest and is acquired during or after administration into the fluid of contrast agent by the power injector at a current contrast agent flow rate according to the current injector setting;
  a fluid property determiner configured to determine, by using in-image information of the current one or more image, a physical property of the fluid;
  a power injector setting determiner configured to determine a desired contrast agent flow rate based on the current fluid property;
  an adjustment back-end configured to interface with the power injector for re-adjusting the power injector setting to effect the desired flow rate.

According to one embodiment, the physical fluid property is a current fluid flow rate. According to one embodiment the power injector setting determiner is configured to determine the desired contrast agent flow rate to be below the current fluid flow rate. More specifically and according to one embodiment the desired contrast agent flow rate is determined as a pre-defined percentage value of the current fluid flow rate of the fluid. Percentage values in the region of 30%-40% have shown to yield satisfactory results for human or animal blood and for example Iopamidol (eg, Iopamiro 300 by Bracco, Milan, Italy) as contrast agent but use of other contrast agents are also envisaged.

According to one embodiment the controller comprises a fluid flow analyzer configured to determine a vector field of the fluid flow (velocity field) at the region of interest based on one or more follow-up images acquired by the imager whilst the power injector administers contrast agent at the determined desired flow rate.

The controller as proposed herein allows for an automatically adaptive contrast agent injector system. But unlike conventional systems, the controller is not merely configured to improve image quality as such so as to effect production of images a human beholder would want the image to be. In that later scenario it is the more contrast the better. In distinction thereto the configuration of the controller as proposed herein is to enable precise and reliable velocity field determination or analysis from images. The controller in one embodiment is two-stage. In a first stage a preferably scalar characterization of the fluid (which includes as an admixture the added contrast agent) is determined. The injector rate is controlled so as to remain low relative (expressed as a suitable percentage value) to the determined or estimated fluid flow rate. Fresh images with the re-adjusted injector rate are acquired if the injector rate was higher than permitted. It is then those freshly acquired images on the bases of which the fluid's velocity field is then determined or computed in the second stage at a user selectable ROI. This yields accurate and stable results that accommodate sudden changes in the flow characteristic of the fluid. One area of application is hemodynamics to better understand the velocity fields of human or animal blood with contrast agent added in an angiography. The correct position of a flow diverter can be checked by using the computed velocity vector field to characterize the hemodynamics at a region of interest. The determined desired contrast agent injection flow rate is essentially a variable upper threshold that accounts for changes in the fluid's behavior and controlling the injection rate to remain below this threshold has the benefit that the influence of the contrast agent's presence on the blood or other fluid's dynamics is kept relatively low. This is one reason why the subsequent vector field determinations based on images acquired at the reduced injection rate are so reliable.

According to one embodiment the controller still makes use of the image contrast because the controller includes in this embodiment an image contrast determiner configured to measure an image contrast in the current image or in the one or more follow-up images, the adjustment back-end configured to interface with i) the power injector for re-adjusting the power injector setting to effect an increase of the contrast agent flow rate if the determined contrast is below a pre-defined contrast threshold or the adjustment back-end is configured to interface with ii) the imager to adjust radiation dosage.

According to this embodiment, the controller operates to reconcile two competing concerns: one is to keep the image quality (contrast) at a minimum. Contrast varies directly with the contrast agent injection rate used by the power injection. The other concern is, however, to keep the influence of the injected contrast agent on the blood flow as small as possible. In other words the controller operates to compute the above mentioned upper threshold in relation to the flow rate and a lower threshold in respect of the contrast in the images. The flow threshold is "upper" in the sense that violation causes the controller to decrease the injector rate. On the other hand, the "contrast" threshold is "lower" in the sense that violation causes the controller to increase the injector rate.

In one embodiment it is only the upper threshold that is computed. Preferably, however, both thresholds are computed and to so curb the contrast agent flow rate from above and below.

According to one embodiment the fluid is pulsatile (such as arterial blood) and the physical flow property is the fluid's pulsatility. In this embodiment, the fluid property determiner operates to determine a flow pattern of the fluid. Specifically the fluid property determiner is configured to measure pulsatile modulation across the one or more image, possibly including the one or more follow-up images. Said measurement is based in one embodiment on contrast in the images. In this embodiment, The adjustment back-end is configured to interface with the power injector for re-adjusting the power injector setting to effect a decrease of the contrast agent flow rate if the measured contrast based pulsatile modulation is below a pre-defined pulsatility threshold. In other words, in this embodiment an additional upper threshold is computed and enforced but here the pulsatility is used as a measure to describe the dynamics of the fluid mixture of contrast agent and blood. A weighted average of the two upper thresholds may be formed or the minimum of the two can be selected so that the desired target threshold is a combined upper threshold. In one embodiment the amount of pulsatile modulation is determined based on a single one of the one or more image or is based on a sequence of at least two images.

The so combined two upper thresholds can be used with or without the contrast threshold forming the lower threshold.

In one embodiment the system's controller is capable of controlling not only the contrast agent flow rate but also the radiation dosage of the imager. This allows breaking a conflict in case the upper and lower thresholds contradict each other.

In an alternative embodiment, the fluid property determiner operates to determine the amount of the pulsatility in the fluid instead of the flow rate. In this alternative embodiment, the power injector setting determiner is then configured to determine the desired contrast agent flow rate based on the determined degree of pulsatile modulation. The adjustment back-end then interfaces, as in the fluid flow rate embodiment, with the power injector for re-adjusting the power injector setting to effect the desired flow rate.

Generally, in this alternative embodiment the controller acts to reduce contrast agent injection rate to ensure that not too much of the underlying pulsatile modulation is lost. This alternative embodiment of the controller can be put to use where an algorithm for fluid characterization is run that depends on the amount of pulsatile modulation rather than the fluid's flow rate. The amount or degree of pulsatile modulation can be measured and quantified as an index (that is, a number) by those algorithms, based on the one more image of the object with the contrast agent. A pre-set value for the amount of pulsatile modulation can be used as an alternative upper threshold for the fluid flow rate based threshold of the other embodiment introduced earlier in this summary.

In one embodiment, the controller is switchable by the user to either determine the flow rate or the amount of pulsatility in the fluid.

According to one embodiment the image or the one or more follow-up images is or are displayed on a screen, the controller comprising a graphical user interface generator or controller for generating on said screen a graphical user interface configured to allow a user to select in the displayed image a sub-image, the flow rate determiner and/or image contrast determiner configured to determine in response to the user selected sub-image the current fluid flow rate by using in-image information only in the sub-image. This allows focusing in more detail on small ROIs to save CPU time or to yet increase further the stability of the determination of the time varying velocity field of the fluid.

According to one embodiment, initially, the power injector administers the contrast agent in a ramp-up phase wherein the contrast agent flow rate rises essentially linearly with pre-defined slope, wherein the controller operates during this ramp-up phase to determine the desired contrast agent flow. This allows the controller to operate without the need for extra image acquisition runs for calibration.

According to one embodiment a graphics display controller is configured to display on a screen a graphic depiction of the computed fluid (velocity) vector field as computed by fluid flow analyzer. This allows visually examining the velocity field.

The system is a closed loop feedback controller in the sense that its output, which is an updated contrast agent injection rate, affects or influences the pixel information in the images acquired when this injection rate is used, if the one of the thresholds, in particular the upper, is violated.

At the same time the images so affected are then fed back into the controller to possibly readjust the contrast agent flow rate.

A communication link between the X-ray equipment, the contrast injector and the controller can be wired or wireless or a combination of both. For example controller communicates wirelessly with the power injector but is wired to the X-ray imaging equipment.

According to one embodiment the adjusted injection rate or rates and contrast agent usage is communicated (for example by display on the screen) to the overseeing clinician for safety reasons.

In embodiment the one or more image or stream or sequence of images are X-ray projection image including "angiograms". However it will be appreciated by those schooled in the art that the proposed controller may also be used in CT or MR angiography. The images may be digital or analog for example as used in analog X-ray image intensifier TV systems.

The term fluid includes "arterial" blood or venous blood. It will be understood herein that other body fluids (other than blood) or fluid mixtures may be investigated by using the controller as proposed herein. In other fluid dynamic contexts, other upper/lower thresholds may be used for example the upper threshold may reflect whether the fluid is laminar or turbulent and controller is configured to ensure the relevant fluid remains laminar or remains in the turbulent phase.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
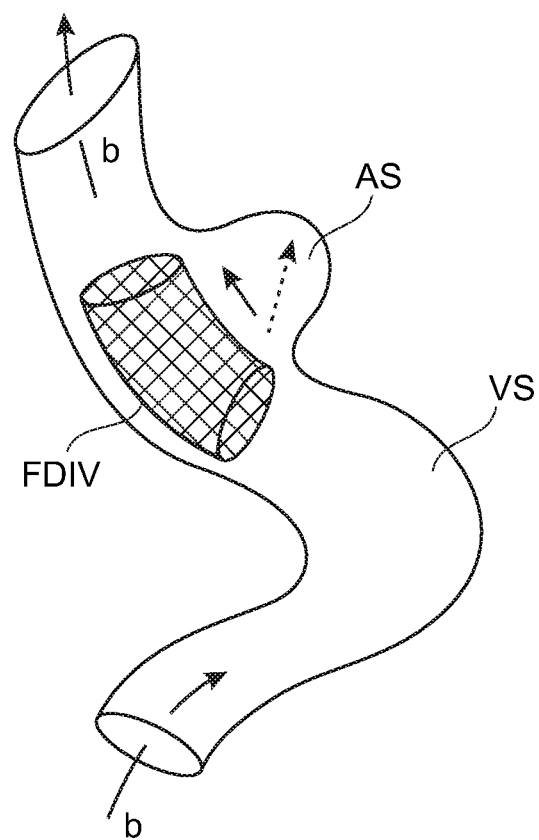
FIG. 1 affords a schematic view of a human or animal vessel.

With reference to FIG. 1 there is shown a vessel VS, for example a human or animal carotid artery inflicted by an aneurysm AS. An aneurysm AS is essentially a "pocket" in the vessel's V wall. If untreated the pocket may grow larger, with its wall thinning out which ultimately may lead to rupture. The blood flow desirable as it may be (indicated in FIG. 1 by arrow 'b') also causes unfavorable pressure to so foster growth of aneurysm pocket AS. An unfavorable blood flow component is indicated schematically in FIG. 1 by a dashed arrow.

In order to pre-empt or at least mitigate such unfavorable flow components, a flow diverter FDIV is implanted into the vessel V. Minimal invasive surgery methods can be used to this effect where the flow diverter FDIV, essentially a stent, is threaded by way of a catheter through an entry point into the body and to the desired position, that is, in this case proximal to the aneurysm AS. The flow diverter stent is a tubular structure made from a fine mesh. It allows an essentially unobstructed blood flow longitudinally through the stent as indicated in the Figure by solid arrows but flow diverter stent ideally substantially weakens or mitigates flow components directed across and into the aneurysm as shown by the dashed vector arrow.

Once flow diverter has been placed and deployed, it needs to be checked whether diverter FDIV serves the above described purpose. To this effect a stream ("run") of X-ray images (or other images based on other types of radiation) are acquired of the relevant region of interest ROI, that is, in this case the area around the aneurysm AS.

Said images are obtained over a certain period of time, and they can then be analyzed to obtain a vector field that describes the blood flow in the relevant region of interest ROI. This vector field can then be used to check the efficacy of the installed fluid diverter.

Figure 2:
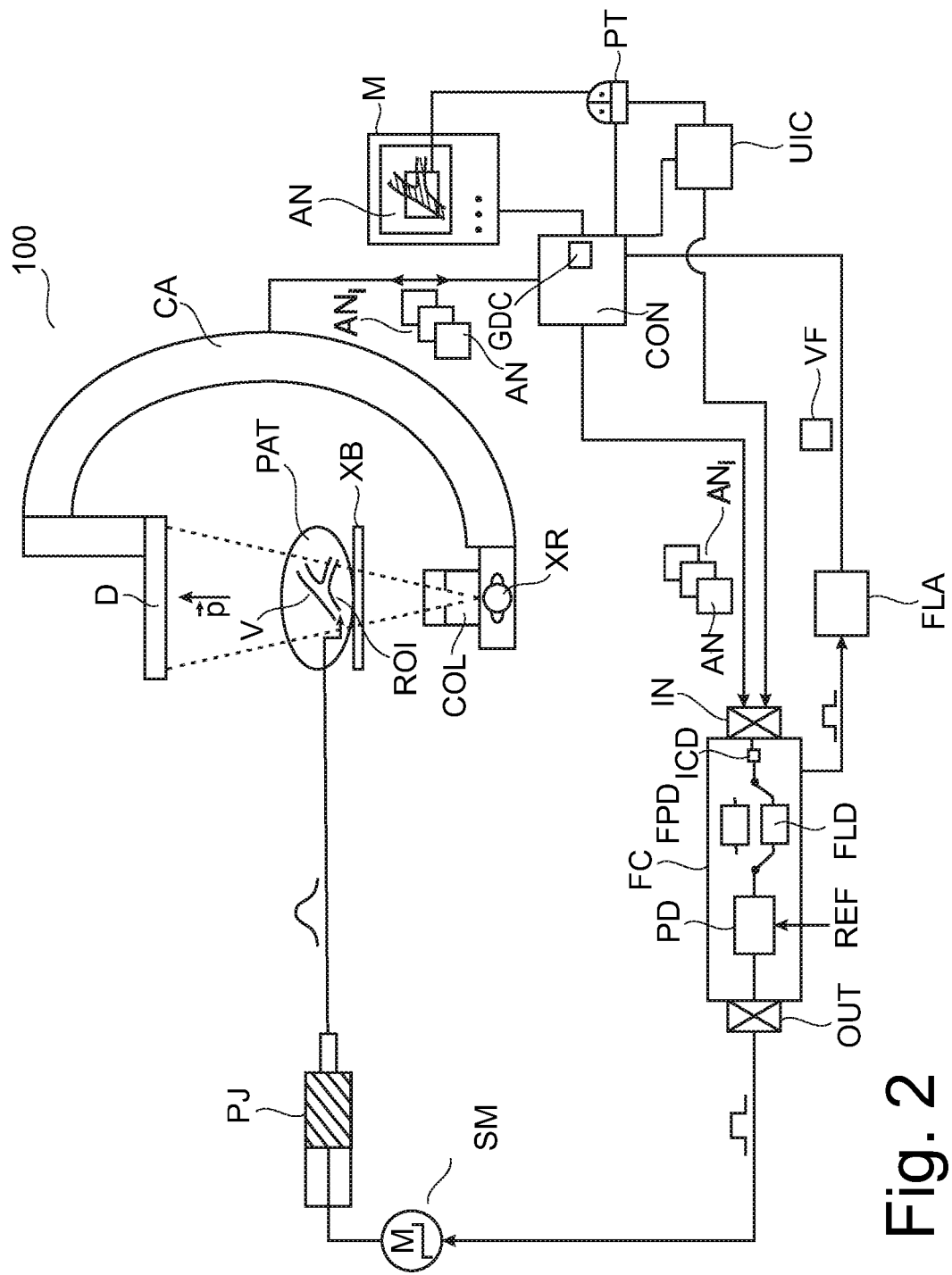
FIG. 2 shows an imaging arrangement including a power injector and a control device to control said power injector.

With reference to FIG. 2, there is shown an arrangement that can be used to obtain information on the blood flow vector field at the ROI. The arrangement includes an X-ray imager 100 and a power injector PJ. FIG. 2 shows the imager 100 of the C-arm type; however it is understood that other imager constructions may also be put to use.

Imager 100 includes a rigid C-arm CA having affixed thereto at one of its ends a detector D, and to the other an X-ray tube XR and a collimator COL (hereinafter together referred to as the C-X-assembly). X-ray tube XR operates to generate and emit a primary radiation X-ray beam p whose main direction is schematically indicted by vector p. Collimator COL operates to collimate said X-ray beam in respect of a ROI.

The position of the arm CA is adjustable so that the projection images can be acquired along different projection directions p. The arm CA is rotatably mounted around the examination table XB. The arm CA and with it the CX assembly is driven by a stepper motor or other suitable actuator.

Overall operation of imager 100 is controlled by an operator from a computer console CON. Console CON is coupled to a screen M. Operator can control via said console CON any one image acquisition by releasing individual X-ray exposures for example by actuating a joy stick or pedal or other suitable input means coupled to said console CON.

During the intervention and imaging an examination table XB (and with it a patient PAT) is positioned between detector D and X-ray tube XR such that the lesioned site or any other related region of interest ROI is irradiated by primary radiation beam p.

Broadly, during an image acquisition the collimated X-ray beam PR emanates from X-ray tube XR, passes through patient PAT at said region ROI, experiences attenuation by interaction with matter therein, and the so attenuated beam PR then strikes the detector's D surface at a plurality of the detector cells. Each cell that is struck by an individual ray (of said primary beam PR) responds by issuing a corresponding electric signal. The collection of said signals is then translated by a data acquisition system ("DAS"—not shown) into a respective digital value representative of said attenuation. The density of the organic material making up the ROI determines the level of attenuation. High density material (such as bone) causes higher attenuation than less dense materials (such as the vessel tissue). The collection of the so registered digital values for each (X-) ray are then consolidated into an array of digital values forming an X-ray projection image for a given acquisition time and projection direction.

Unfortunately, image structures representative of anatomic structures such as blood itself and vessel tissue, are not normally discernible from an ordinary X-ray image without further preparation. This is because said anatomic structures lack the requisite radiation opacity. To address this, an imaging technique has been devised called angiography. In an angiography a sequence of X-ray images (angiograms hereinafter referred to as "angios") are acquired whilst a previously administered contrast agent is required to reside at the region of interest ROI. The contrast agent is essentially a "dye" or a radiation opaque fluid, which is administered to the patient manually or preferably by the power injector PJ to so at least temporarily confer, for imaging purposes, the much needed radiation opacity.

In very simple terms and as indicated in FIG. 2, the power injector PJ operates as a piston-cylinder arrangement. The piston runs inside the cylinder and is energizable by a motor SM, for example a stepper motor MS, to displace the contrast agent fluid that resides in the cylinder to eject same at an adjustable contrast agent flow or delivery rate.

The so administered volume of contrast agent enters the body via a catheter at an entrance point and is carried with the blood flow to the region of interest ROI. Once sufficient perfusion by the contrast agent of the region of interest ROI occurs, a sequence of angios $AN_i$ are then recorded (preferably at a frame rate of at least 30 frames per second) by the X-ray imager 100 and it is those sequence of angios that can then be evaluated and processed to learn about the blood vector field at the ROI. Blood flow velocity vectors are detected from image information in the angiography sequence. According to one method a flow descriptor "Mean Average Flow Amplitude (MAFA) ratio" is computed from the fluid velocities as described in V. M. Pereira et al, "A DSA-Based Method Using Contrast-Motion Estimation for the Assessment of the Intra-Aneurysmal Flow Changes Induced by Flow-Diverter Stents", Am J Neuroradiol, November 2012. The ratio can then be used to assess or validate the effectiveness of flow diverter treated aneurysms. The method is an optical-flow type algorithm. The algorithm tracks the propagation of variations in image intensity through the vascular structure and is able to provide 2D time-dependent velocity vectors. A good overview of X-ray images based velocity measurements can be found in S. D. Shpilfoygel et al "X-ray videodensitometric methods for blood flow and velocity measurement: a critical review of literature," Med. Phys. 27, 2008-2023 (2000).

Desirable as it may be in terms of radiation opacity and the associated high contrast in the angios, the intravascular presence of contrast agent has also disadvantages. One is that the contrast agent itself actively modifies by its mere presence the blood flow one wishes to measure. For example it must be ensured that the flow pattern or the fluid vector field behavior, which one wishes to study, stems only from the vascular structure and hemodynamics itself and is not the result of the contrast agent injection. The angiographic contrast agent should mix well with the blood to achieve this. It has been observed that to obtain results on the fluid vector field with good fidelity the contrast agent injection rate should be well below the blood flow rate at the locality of interest. On the other hand, and as a competing requirement to the above, the contrast agent injection rate should also be sufficiently high in order to obtain good image results, that is, enough opacity should be conferred to the ROI in order to achieve sufficient image contrast. However the blood flow rate is precisely what is not known, so previously the contrast agent injection rate has been chosen and recourse has been had to statistical data and the rule of thumb for suitable injection rates.

It has been observed in experiments conducted by the applicant that fixed contrast agent flow rates result in strongly variable results when evaluating the fluid vector fields. This volatility is even observed for the same patient re-imaged within a relatively short period of time of about an hour. It is suspected that this behavior is due to an inhomogeneous mixing behavior between contrast agent and blood flow rate because the blood flow rate itself is not constant and is subject to abrupt changes caused by factors such as vasodilation or contraction.

In order to ensure high quality and fidelity fluid vector field determinations at the desired ROI, the arrangement in FIG. 2 includes a controller FC. Controller FC is arranged as a closed-loop feedback controller that operates between the power injector PJ and the X-ray imager.

Broadly speaking, the closed-loop controller FC interfaces with power injector PJ and interrogates for the current or live injection rate. Said current injection rate is then processed as will be described in more detail below by analyzing the current angiographic image stream $AN_i$. Controller FC operates to reconcile the two previously mentioned competing requirements of having i) not too much and ii) not too little blood contrast agent flow. To achieve this controller FC acts so as to ensure that an upper and/or lower dynamic threshold associated with contrast agent administration is or are respected. The manner, in which said thresholds are derivable from a current angio acquired at the current injection rate will be explained below in detail. If the controller FCI determines that the current injection rate causes violation of the one or two thresholds, controller FC operates to compute a new, updated target injection rate and forwards same to the power injector PJ via suitable interface means to effect the re-adjustment of the current contrast agent injection rate to the new contrast agent injection rate, thereby completing the feedback loop.

If the one or two thresholds are not violated for the current contrast agent rate or the pump PJ has been adjusted to now operate at the computed target flow rate, a corresponding signal issued by controller FC to a fluid flow analyzer FLA. Said analyzer FLA then takes in the now acquired sequence of angios AI and it is those angios on which the subsequent fluid vector field analysis is going to be based. The computed fluid vector field can then itself be visualized in a vector field image VF which can then be forwarded to the console CON to effect display on a screen M alongside or instead of the current one AN or instead of a user-selectable one of the angios $AN_i$. The console runs a suitable graphics display controller GDC to connect with a graphics card of console effect display and rendering of velocity field on the screen.

Operation

The closed-loop feedback controller FC includes the input port IN, an optional image contrast determiner ICD, and a fluid property determiner to determine a physical property of the fluid. The fluid property determiner is configured to operate as a flow rate determiner FLD and/or as a flow pattern determiner FDP. Controller FC also includes a power injector setting determinate PD and an adjustment back-end OUT.

As mentioned briefly above, controller FC is configured to reconcile the two above mentioned competing considerations in respect of contrast agent flow rate and image quality. To this end controller FC is configured to compute the two thresholds (upper) and lower), referred to hereinafter as the "flow threshold" and the "intensity threshold", respectively. According to one embodiment, it is only the flow threshold that is computed or the controller FC is switchable (by user request) to compute only the flow threshold.

According to one embodiment those two thresholds, or at least one of those thresholds are computed dynamically throughout the course of the intervention, that is, they vary rather than being computed up-front as static threshold to cope with the inhomogeneity caused by the change in the blood flow itself. In simpler embodiments however, one or both of two thresholds is static, so it is not adapted throughout the image acquisition run to improve responsiveness and save CPU time.

Turning now first to the flow threshold, controller FC operates briefly as follows: Injector PJ injects the contrast agent at an initial contrast agent flow rate. After a short run-up period (to allow the contrast agent to reach the region of interest), the image acquisition run is initiated to acquire a sequence of angiograms $AN_i$ of the region of interest.

The blood flow rate is then calculated from the angio sequence by the FLD. The new updated contrast agent injection flow rate is calculated by the PD as a percentage of the calculated blood flow computed in the previous step. If the initial flow rate is at or below the so computed updated flow rate, said initial flow rate is maintained. If not, the updated flow rate is used instead to control the power injector PJ.

As mentioned, this newly updated injection rate for the contrast agent is either kept constant throughout the remainder of the acquisition run and is then adapted only for any new run or is updated within the course of a given image run. "Image run" as used herein are understood to mean a sequence of images that are acquired at a set frame rate but otherwise uninterrupted throughout a period of time.

As the blood rate may vary over time, it is preferable that controller FC acts to effect adjustment of the injection rate continuously. In other words, re-adjustment action is clocked to be executed repeatedly at pre-defined time intervals, based on the measured blood flow rate during the remainder of the run, or is clocked to adjust the injection rate only when the increase or decrease of blood flow has exceeded the flow threshold value since an initial measurement.

In other words, the injection rate is
i) kept at constant throughout the run if, at an initial determination, the rate is found not to violate the flow threshold or the intensity threshold, or
ii) is dynamically adapted at pre-defined interval to better cope with highly inhomogeneous flow behavior, or
iii) only adapted once the flow threshold is exceeded.

According to one embodiment, the controller is FC is configurable to operate in either one of the three modes i)-iii).

According to one embodiment the imager's 100 frame rate is about thirty frames per second (fps).

According to one embodiment the flow determiner FLD is based for example on an optical flow type algorithm. In other embodiments, an indicator-dilution (Steward-Hamilton) method or time-density or distance-density curves based methods may be used at this stage. In a preferred embodiment, flow determiner FLD operates to determine the blood flow rate as a scalar value instead of or by using vector fields. This is because the blood flow determination by flow determiner FLD is not end of itself for present purposes, but it is a preliminary step to ensure that flow field analyzer FLA can then compute in a second stage or phase the flow vector field of the blood flow at the required accuracy. This two stage approach affords more reliable or stable results because the single average scalar value captures a more global overall fluid behavior, i.e., does not suffer so much from local inaccuracies as computation solely based flow vector fields would. Of course according to one embodiment the blood flow values as computed by FLD may still be displayed on screen M alongside the currently viewed angio AN, or in a pop-up GUI window upon user request. In other words as proposed herein, the blood flow scalar value is determined first and the computationally more expensive computation of time-dependent vector fields is relegated to the FLD and executed only once the contrast agent flow rate is as computed as set below to ensure accuracy and fidelity of the vector field computations.

In optical flow type algorithms, flow rate determiner FLD essentially compares and tracks intensity pixel values of corresponding pixels across the subsequent images in the sequence $AN_i$. Difference equations between the intensity pixel values are then approximated by a Taylor-series expansion which can then be solved numerically to arrive at the flow rate.

The blood or fluid flow rate as determined by flow rate determiner FLD can be output in a multitude of parameters. According to one embodiment the ROI is an artery so it is arterial blood flow that is of interest. Arterial blood flow however is pulsatile and to account for this the blood flow values or parameters can be determined as:
  the average blood flow value measured over a time interval
  the maximum blood flow value measured over a time interval
  the average blood flow value measured over a time interval restricted to a cardiac cycle, or a number of cardiac cycles
  the maximum blood flow value measured over a cardiac cycle Because blood flow is different in different vessels, and even in different locations of the same vessel, the measurement can be based on a user-selected region-of-interest, or on an average or maximum value of the whole image. For example, according to one embodiment the user interface controller UIC receives an image portion defined by the user tracing out a rectangle or circle bounding the region. The tracing can be done through pointer tool action PT or by touch-and-swipe action for embodiments where screen M is a touch screen. Spatial pixels so specified in the image plane are then translated into coordinates which are forwarded to FLD via user interface controller UIC. Flow determiner FLD uses the received co-ordinates as constraints to spatially constrain the region through which the blood flow rate is to be determined.

As a default flow rate determiner FLD operates across the whole vessel "footprint" (that is, the image portion representative of the projection view on the vessel) for each of the angios. To this end, in one embodiment an intensity pixel value thresholding is executed in order to base the blood flow determination only on image pixels with an intensity above a user definable threshold. This is to ensure that the determination of the blood flow rate is based only on pixel values that stem from the contrast agent imparted opacity, in other words, on pixel values that are representative of a region within the vessel.

According to one embodiment it is not the angios themselves that are used but they are pre-processed to compensate for highly radiation opaque structures naturally occurring in the body such as bones. The usual DSA (digital subtractive angiography) techniques can be used which are based on a reference fluoroscopic image ("fluoro"). The reference fluoro is an X-ray image acquired when no contrast agent is present. Said reference fluoro is then subtracted pixel-wisely from each of the acquired live angios to cancel out the contribution for said structures of high radiation opacity.

Figure 3:
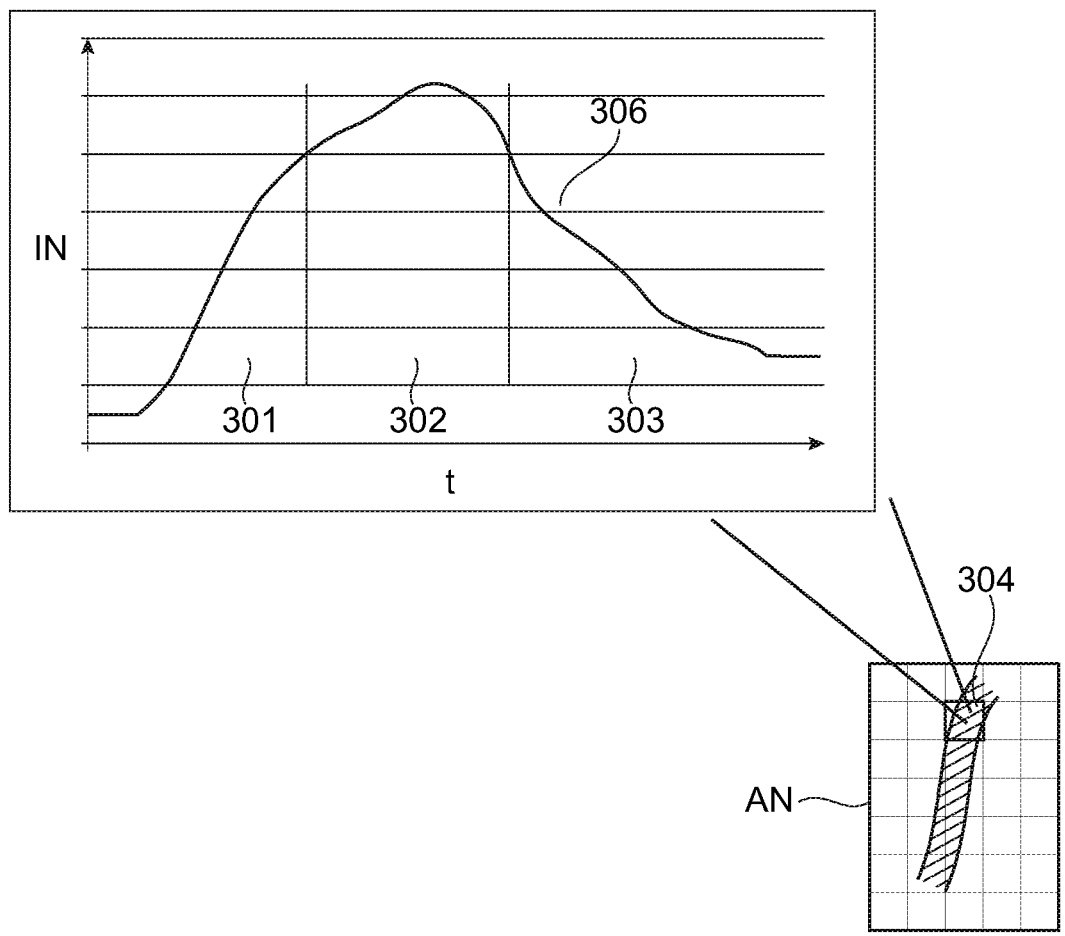
FIG. 3 shows phases of a local intensity vs. time curves of an angiogram.

Reference is now made to FIG. 3 which shows a pixel intensity-versus-time curve 306. Curve 306 is taken relative to a fixed image portion 304 (including a plurality of pixels) on the image plane of one of the angiograms AN in the sequence $AN_i$. As can be seen in FIG. 3, once the volume of the administered contrast agent reaches that part of the ROI that corresponds to the pixel element 304, the intensity at that pixel will increase in a "ramp-up" or linearly rising phase 301. The intensity will then remain relatively constant in an operation phase 302 at a pre-programmed initial rate and will a then drop-off in a final phase 303. In other words a power injector PJ needs a certain time during the ramp-up phase to actually operate, that is, administer contrast agent at the pre-programmed initial injection rate. Controller FC as proposed herein is configured in one embodiment to compute the updated blood flow rate already during that ramp-up phase. In this way no extra image runs have to be conducted, thus saving X-ray dose and contrast dose, while at the same time the normal angiography workflow can be adhered to. In some embodiments the execution of the above described computation of the updated contrast agent flow rate is user-controlled and is triggered by the user operating suitable actuation means such as hitting a key on a keyboard connected to console CON or by operating a "go" GUI button displayed on screen M.

Once the blood flow value is obtained either based on a sub image (local option) or based across the whole vessel footprint for each angio (global option), said blood flow rate is then forwarded to injector rate determiner PD. Injector rate determiner PD applies a pre-set percentage value to be the blood flow rate to compute a new desired target contrast agent flow rate.

According to one embodiment said percentage value is pre-set by the manufacturer but in other embodiments the user can access a set up or "config" menu to manually fine tune the percentage value. Adjustment back-end OUT has a suitably programmed interface to connect with the input port (not shown) of power injector PJ to readjust accordingly to the newly computed contrast agent flow rate, if the current injection rate is above the computed target flow rate. Configuring adjustment back-end to co-operate with a given programmable power adjuster can be usually be done by obtaining power injector manufacturer's specification which allows programmers to develop a suitable application program interface API. According to one embodiment, back-end OUT is configured according to the CANopen standard.

The above described loop closes by receiving at the input port IN newly acquired projection images $AN_{i+k}$ which are then processed similarly as described above for any initial angio sequence $A_i$ to so dynamically compute a sequence of updated contrast agent flow rates each forming an instantaneous upper threshold for the contrast agent flow rate. Back-end OUT then forwards said sequences one at a time to the power injector to adapt, if need be, the contrast agent flow rate accordingly throughout the image run.

Having explained earlier how the flow threshold is gotten, it will now be explained how controller FL operates to compute the lower threshold, namely, the intensity threshold.

The amount of contrast agent affects the image quality of the acquired X-ray images. If the amount of contrast agent is too little this results in a poor contrast of the vessel structure in the X-ray images and might not allow for valid flow estimation. Therefore controller FC includes in one embodiment the image contrast determiner ICD configured to determine the contrast in the image AN. The controller FC operates by respecting a lower threshold on the image intensity and raises the contrast agent injection rate to ensure that contrast does not drop below a pre-set contrast threshold. This intensity should preferably be measured after subtraction of a mask-image or reference fluoro, so that only the intensity of the vessel VS's footprint is measured and taken into account and not that of, eg. bones. The average intensity can be established given a certain color or gray value depth for the acquired images AN which according to one embodiment is 16-bit: the highest possible signal for a detector D cell is encoded by 65535 (which is normally mapped to "white") and the lowest possible signal is encoded as is 0 (which is usually mapped to black). High attenuation means a low signal. To quantify signal lowness, according to one embodiment, an average intensity value across the vessel footprint is registered and the ratio between said average and the depth range is formed. For instance, using the 16-bit example, if an average value of 10000 is measured across the pixels in the vessel footprint, the signal has a lowness of $(65535-10000)/65535 \approx 85\%$.

The intensity threshold cannot be used directly to compute the updated injection rate since the signal gain for higher or lower injection rates is not known. The intensity threshold rather serves as quality check or "filter" and the computations in respect of the upper flow threshold will be executed only if the image quality of the received angio $AN_i$ stream satisfies the (lower) intensity threshold.

According to one embodiment, controller FC varies the injection rate to so establish the minimum required contrast injection rate. In one embodiment, the sequence of angios $AN_i$ is acquired by X-ray image 100 whilst power injector injects at the pre-programmed initial inject contrast agent flow rate. Controller FC then reads in one AN or more angios from the sequence $AN_i$ and measures the pixel intensities and interrogates for the current injection rate. If the measured intensity is found too low, the injection rate is increased. If intensity is found too high, the injection rate is decreased. The described contrast agent flow rate adjustments are repeated for a fixed time period, or until the difference in intensity between the lowest injection rate yielding acceptable intensity and the highest injection rate yielding unacceptable intensity is smaller than a predefined threshold. Since a new programmed injection rate may not be attained immediately by the power injector, the power injector communicates the actual current injection rate to the controller FC via interface IN.

The intensity measure provides a lower threshold on the contrast injection rate, whereas the blood flow rate computed as explained above provides the upper threshold on the contrast injection rate. The two thresholds can be used together to establish a new injection rate, for example by taking the average of the associated two injection rates if either threshold is violated.

On occasions it may happen that the two thresholds, that the (upper) flow threshold and the lower (intensity) threshold contradict each other. In other words it may turn out that the calculations dictate that the upper threshold is actually lower than the lower threshold. To cope with such a scenario, controller FL includes according to one embodiment a logic module to detect and resolve this inconsistency. If the logic module registers that the upper intensity threshold drops below the lower flow threshold this is flagged up. Process flow then switches over and controller FC then interfaces via its back-end OUT or via a different output port with X-ray imagers 100 instead of with power injector PJ to effect adaptation of the X-ray dose intensity. For example, if the contrast injection rate is found too high according to the computed blood flow rate, but cannot be lowered because of the low signal, that is, too low pixel intensity in the angios AN of the current sequence, controller FC acts to have the X-ray dosage increased. In particular this allows the user to set the contrast injection rate to a low percentage of the blood flow rate. However this comes at the expense of higher X-ray dose to obtain high quality vector fields.

In short, the two thresholds can be used together to monitor the quality of the injection for the purpose of blood's velocity vector field determination during the acquisition, and controller FC is configured to adapt the contrast injection rate and/or X-ray dose if necessary.

According to one embodiment, controller FC includes instead of in addition to flow determiner FLD the flow pattern determiner FPD. Flow pattern determiner FPD is configured to monitor a further aspect of the blood flow that is caused by the injection of the contrast agent as will now be explained. If the amount of injected contrast agent is too high this will also change the hemodynamic behavior of the accumulative flow, that is, of the fluid mix of contrast agent and blood. Normally, that is when left undisturbed, arterial flow is pulsatile. But if the flow of the mix is merely driven by the injected contrast volume itself, no or very little pulsatile modulation will be left. The lack of pulsatile modulation can present a problem for the fluid vector field computation. For example in O. Bonnefous et al ("Quantification of arterial flow using digital subtraction angiography, Med Phys. 39 (10), October 2012), the modulation of contrast creates patterns that are detected and tracked to obtain flow information. But if there is no modulation then the vessel footprint pixel intensity will be relatively homogenous throughout X-lack flow patterns caused by the pulsatile modulation. Said patterns will be hidden by the domineering contrast agent flow and hence there are no patterns that can be tracked.

In the one embodiment it is therefore not only the intensity that is taken into consideration for the (upper) flow threshold but also a score is computed to account for the extent to which the contrast agent injection rate influences the hemodynamics behavior of the accumulative blood flow that is, the fluid mixture formed from the blood and the resident contrast agent. Although the described change in hemodynamics may present difficulties for same flow calculation algorithm, it is the change in hemodynamics itself that is detected from the angios and that is then quantified or measured. This measure forms a third parameter that is used to control the contrast injection rate and which the flow pattern determiner FPD is configured to register and monitor.

Figure 4:
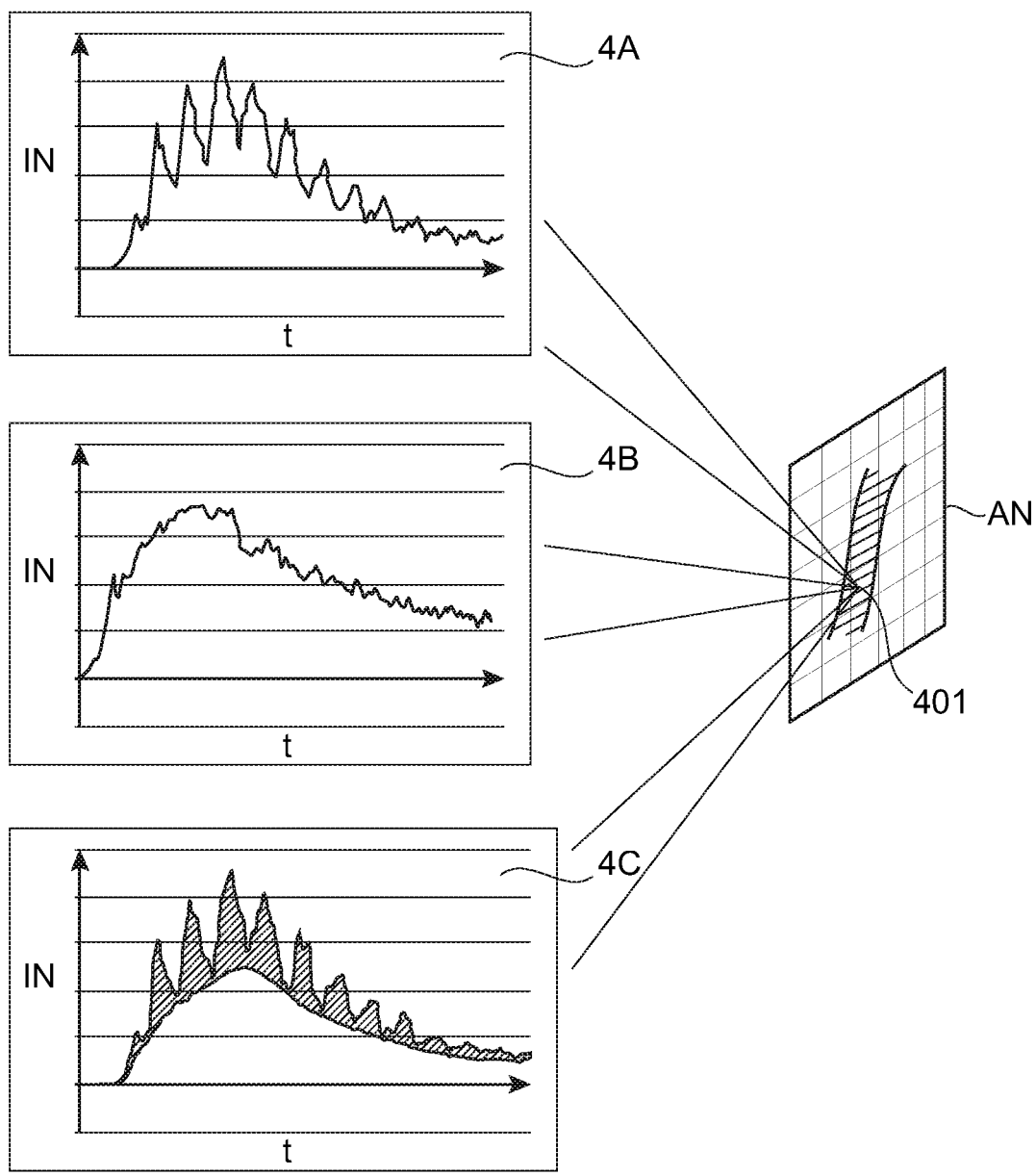
FIG. 4 shows local intensity vs. time curves of angiograms.

Reference is now made to three diagrams 4ABC of FIG. 4 showing intensity vs time curves associated with a single pixel element 401 in an angio AN.

Curve 4A shows a jagged evolution of the intensity, which echoes the underlying pulsatility of the blood flow. In other words, in the situation of FIG. 4A the contrast agent flow as administered by power injector PJ is adjusted so that at least traces of one of the blood's flow characteristic (in this exemplary case its pulsatility) remains.

This is unlike the situation in diagram 4B. Here the intensity vs. time curve shows that the contrast agent flow rate, as administered by power injector PJ, actually "overrides" pulsatility of the underlying blood flow so the characteristics of the blood flow is lost. In other words the contrast agent injection rate as of FIG. 4B is too high so it is undesirable as compared to the more desirable contrast agent rate injection rate as of FIG. 4A. In sum, the transition from a diagram 4A situation to a diagram 4B situation is caused by an increase in contrast agent injection rate, and materializes the change in hemodynamics that should be avoided.

The diagram in FIG. 4C shows an example according to one embodiment as to how this change in hemodynamics can be measured by flow pattern determiner FPD. The amount of modulation (imparted by the blood's pulsatility) that remains in the fluid mixture can be determined, for example, by computing the area under the curve 4A and taking the difference, in absolute terms, between said area and the area under a smoothed version of said curve. Said difference forms a pulsatility index or score which can be compared to a pre-set but user-adjustable pulsatility threshold. The smaller said difference or index, the more of the pulsatility modulation is lost in the instant blood-contrast agent mixture. As can be seen, no additional images need be acquired to establish the pulsatility score or threshold. The difference curve is shown as diagram 4C in FIG. 4. According to one alternative embodiment, the difference is taken between successive local maxima and minima. This is expected to be higher for curve 4A than for curve 4B.

In yet another embodiment, operation of flow pattern determiner FPD is based on distance vs. intensity curves, where image intensity is plotted versus the distance on a vessel. For this approach, first the centerline of a vessel must be calculated by means of a segmentation of the relevant vessel's footprint. Using spline curves to describe the footprint's borders, a centerline can be defined by morphing the borders curves towards each other. The pixel intensity distribution over said centerline can then be established and the amount of hemodynamic changes can be established similar to the approach in relation to FIG. 4. The distance-intensity curve approach requires only a single image, provided that the contrast-injection has started sometime before image acquisition, so that the contrast agent has indeed travelled along with the blood to the relevant vessel. In either embodiment, controller FC operates to return a desired injector flow rate based on computing the pulsatility index of one or more of the angios $AN_i$ and comparing said index with the threshold. The injector rate is adjusted, that is, lowered by a certain amount to ensure the then acquired images evidence an amount of pulsatile modulation at least as defined by the pre-set threshold.

According to one embodiment, controller FC is configured to be switchable (as shown is FIG. 2) between flow rate determiner FLD or flow pattern determiner FPD so operation of controller FC is based on either one or the other. The user can so select whether the upper threshold is to be computed based on blood flow rate or the pulsatility index and the power injector PJ' contrast agent flow rate is adjusted accordingly to the one or the other. It is also envisaged that for an image run, the determination of the desired flow rate for the injector is based on both thresholds. In this embodiment, controller FC switches between the two determiners FLD, FPD in turn. A combined threshold can be obtained by taking for example the minimum of the two injector rates that are associated with the flow threshold and the pulsatility index, respectively. Alternatively a weighted average can be formed and the choice of the weights reflects a priority the user attaches to either of those two upper thresholds. The intensity threshold can be used as the lower threshold if desired.

It is envisaged in one embodiment that the controller FC is responsive to user adjustment interface such as a GUI that accepts user input to set the various thresholds and their combinations and or their weightings.

In distinction to the dual mode controller embodiment described above, according to a simpler embodiment, controller is not switchable so includes either the flow rate determiner FLD or the flow pattern determiner FPD, but not both.

The various embodiments in the combinations thereof as described herein are equally applicable to the alternative embodiment where the flow pattern determiner FPD is included instead of the flow rate determiner FLD.

Figure 5:
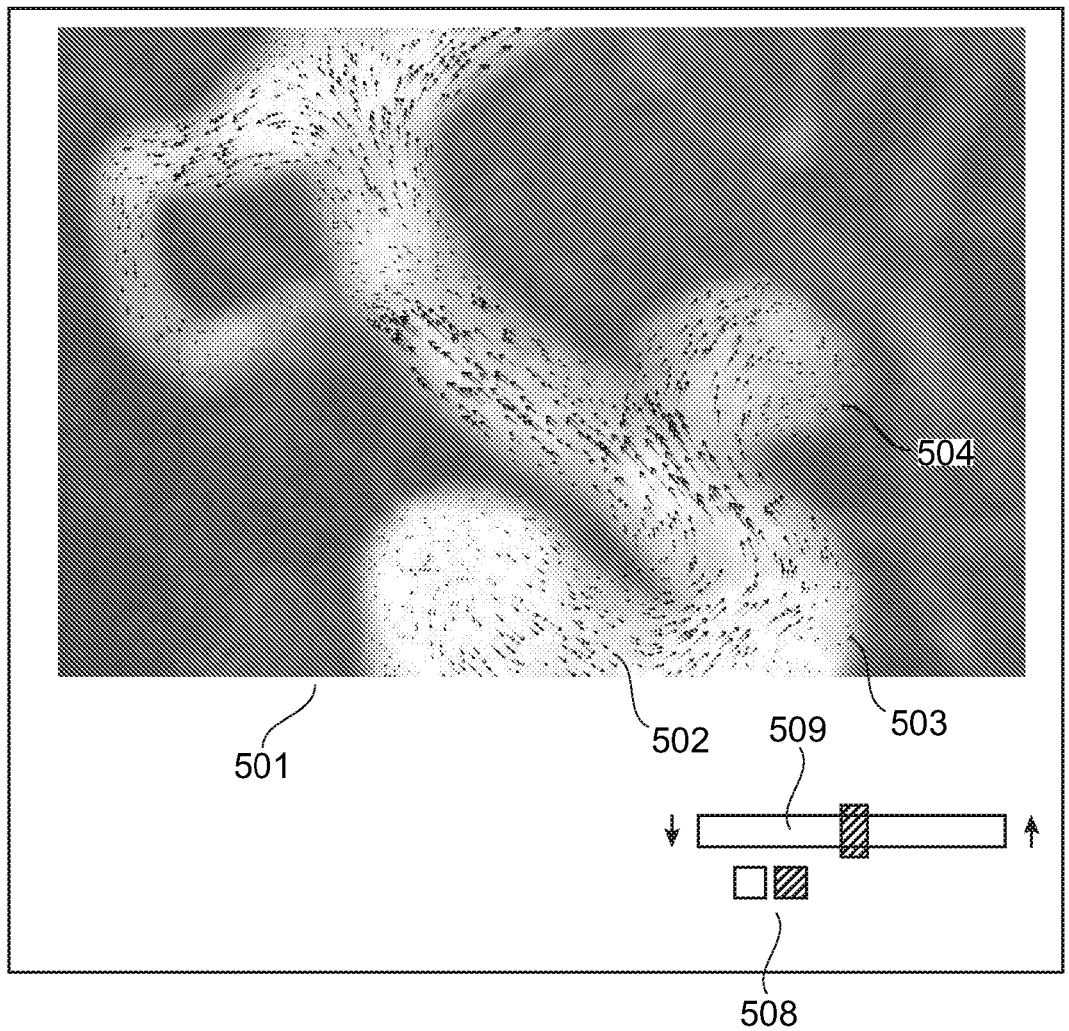
FIG. 5 shows a schematic view of a graphical user interface for analyzing a vector field of fluid.

Reference is now made to FIG. 5, which shows a graphic user interface GUI that includes a graphic depiction of the blood flow vector field as established by analyzer FLA based on images acquired by imager with a contrast agent injection rate that respects the selected combination of the thresholds as described herein.

User interface GUI is produced by a user interface controller or generator UIC. UIC reads in the parameters descriptive of the computed fluid vector field as output by analyzer FLA. The blood flow's velocity vector field data VF may for instance be stored as an associative array where each pixel point co-ordinate is associated with two values: i) the direction of the flow field at that point, and ii) the magnitude of the velocity at that point. There is also a parameter for the time index. User interface controller UIC then cooperates with graphics display controller GDC to render the velocity field information VF into a graphics image including a plurality of arrows or similar directional symbology. In other words, each pixel is assigned a graphic symbol, for example an arrow whose length is proportional to the magnitude of the velocity at that point and its direction corresponds to the computed direction at that point as recorded in the array. At a selection of pixel positions the so computed arrows or similar graphic elements are then overlaid on a representative angiogram. The representative angiogram 501 includes a footprint of the vessel of interest 503. The aneurysm footprint is shown at 504. The vector field is indicated by the plurality of symbologies 502 superimposed on the image portion representative of the footprint 501. According to one embodiment, user interface GUI includes interactive GUI means for example a slider widget 508, and a toggle widget 509.

The widgets 508, 509 are shown overlaid in one embodiment at the lower edge of the image 501 while it is understood that other positions for example above the image or along the sides are also envisaged and the two widgets may not be necessarily grouped together as exemplary shown in FIG. 5.

The toggler 508 allows the user toggling between two grey-or-color encodings of the angio-arrows representation.

Specifically and according to one embodiment, the toggle includes two buttons shown in the FIG. 1 as a light and dark square. When actuating the dark square button, a pixel encoding is effected and displayed that renders high attenuation regions darker than the surrounding tow attenuation issue. This is the usual, default rendering. Upon actuating the other, that is, the light square button, the encoding is inverted (as shown in FIG. 5) is invertible. In other words the vessel footprint 503,504 (shown normally in dark because of the contrast agent) shows now in lighter or a first color or in white than or compared to the surrounding tissue which shows in darker or a second color or in black instead. At the same time and complementary thereto the symbologies 502 indicative of the vector field are shown inverted to the color/gray value encoding of the footprint pixels. For example, in FIG. 5, because the footprint is white the symbology is shown in black (as is currently shown in FIG. 5). Conversely, if the angiogram 503,504 is shown in the usual pixel color/gray value encoding with black for the vessel footprint the directional symbologies 502 would show up white.

In one embodiment slider 508 includes a bar along which a slider button which is slidable over the bar by pointer tool PT action or by touch-and-swipe finger action for a touch-screen embodiment. Slider 508 allows the user to control the density with which symbologies 502 are shown. In other words the number of representative arrows 502 shown per unit area on the image plane can be adjusted in smooth transition depending on the level of detail called for by the task at hand. FIG. 5 shows the situation when the flow diverter is not yet present. Consequently there are flow components directed head-on into the aneurysm putting unfavorable strain on the aneurysm tissue.

According to other embodiments, there are further GUI widgets for navigating the individual angios or images in the current or previous image runs, and/or for changing the length of the arrows 502 and/or the coloring of the individual arrows 502 according to the magnitude of the velocities at the respective point.

According to one embodiment user interface controller UIC is configured to receive a user selectable selection of a sub-image from the angio AN in the sequence $AN_i$ that is currently displayed. By pointer tool PT operation or, for touchscreen embodiments, touch-and-swipe user action or similar, preferably graphical input means, the user outlines a region in the vessel VS's footprint in the currently displayed image AN. This can be done by tracing out a circle or a rectangle. It is then only those pixels with their coordinates inside the outlined region that are taken into account when computing the various upper thresholds (flow or pulsatility) and the lower threshold (contrast). In this way the contrast agent injection rate control operation can be restricted to the region within the vessel where the hemodynamic behavior is to be studied in more detail. By default, it is the whole of the vessel footprint on which the controller's FC operation is based in respect of the two upper and/or the lower threshold.

Figure 6:
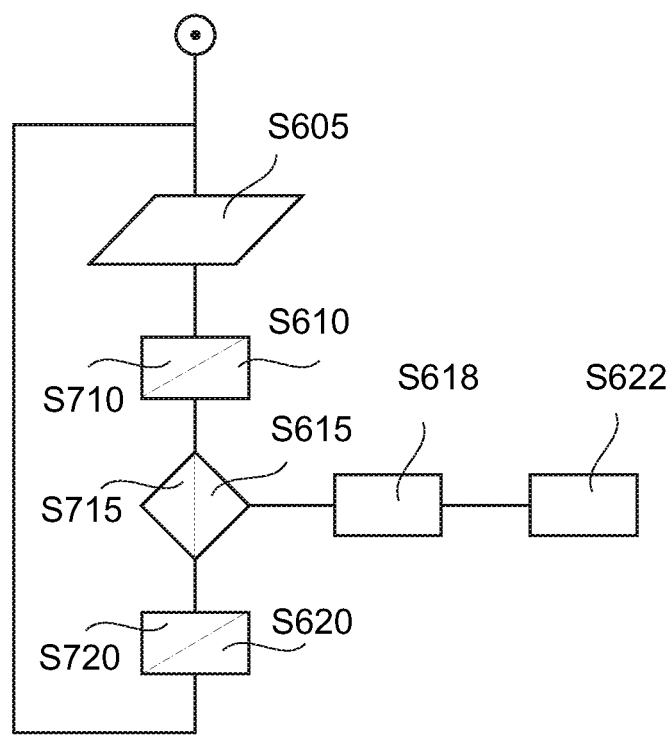
FIG. 6 is a flow chart for an example of a method of controlling a power injector.

With reference to FIG. 6 there is shown a flow chart for a method of controlling power injector PJ.

At step S605, one or more angios are received. The angios were previously acquired whilst a contrast agent is administered at an initial contrast agent injection or flow rate.

At step S610, blood flow rate is determined by using in image pixel intensity information in one or more of angios in said sequence.

At step S615, the initial contrast agent flow rate and the determined blood flow rate are compared. A pre-defined percentage value of the determined blood flow rate is computed. The computed fraction of the blood flow rate is then set as a maximum target threshold for the contrast agent flow rate. It is then checked whether the initial contrast agent flow rate is lower than this threshold. If it is, flow control can pass through to step S618 where the velocity vector field is determined from the acquired one or more angiographic images. At step S622 the so determined velocity vector field is then rendered for display on a screen as a graphic depiction or representation. In one embodiment, the graphic depiction is displayed superimposed on a user-selected one of the angios.

However, if, at step S615 it is determined that the initial contrast agent flow rate exceed said threshold a new desired contrast agent flow rate is determined. The new or updated contrast agent flow rate is set equal to the threshold or to a value below that threshold.

At step S620, the current contrast agent flow rate is readjusted to the new or updated contrast agent flow rate. If a new contrast agent flow rate is used the image acquisition is halted for a certain period of time so as to allow said reduction of contrast agent reduction to take effect at the region of interest. Image acquisition at the new contrast agent injection rate is then resumed and the above steps are repeated to possibly readjust or maintain the updated contrast agent injection rate or flow rate.

According to one embodiment step S616 of determining an upper threshold also includes determining a lower threshold for the initial or current contrast agent flow rate.

According to one embodiment this involves determining average image intensity at an image portion representative of the region of interest. This lower threshold ensures there is enough contrast in the image in the first place. The accuracy of the blood flow determination at step S610 can thus be enhanced.

According to this lower and upper threshold embodiment it is not only checked whether the current or initial contrast agent flow rate is below the previously calculated upper threshold but it also checked whether the currently received images satisfy the lower threshold. If yes, flow control passes to a step S618 to determine the velocity vector field.

If however it is found that the image contrast is below the pre-set lower threshold value an updated contrast agent flow rate is determined in between the upper flow threshold and the current contrast agent flow rate which according to one embodiment is accomplished by taking the average.

According to this embodiment it is this average contrast agent bounded by those two thresholds that is then forwarded to update the power injector's flow rate accordingly.

According to yet another embodiment determining the upper threshold also includes evaluating blood flow characteristics as evident from the acquired sequence of angiograms.

According to one embodiment a flow characteristic, for example the amount of pulsatility modulation, is measured by evaluating intensity versus time curves at pixels forming the footprint of the region of interest. A score value for the pulsatility is established.

According to one embodiment the lower threshold is entirely in terms of the pulsatility index whereas in other embodiments a combined score of the previously mentioned intensity based lower threshold and the pulsatility index is obtained to so form a combined lower threshold.

According to one embodiment the pulsatility index can also be calculated from a single image using distance vs. intensity curves.

According to one embodiment the previous steps S610 through S615 and S620 are executed during a ramp up phase whilst, initially, the contrast agent flow rate linearly rises from substantially naught up to an initial contrast agent flow rate.

According to an alternative embodiment, there is a step S710 instead of step S610, where, instead of determining the blood flow rate, a pulsatility index or score is determined based on the one or more images $AN_i$. The pulsatility index is suitable to measure the amount of pulsatile modulation in the blood (having the contrast agent residing therein).

In this embodiment, at an alternative step S715 it is then determined, based on a pre-defined threshold value for the index and the determined pulsatility index, whether there is a decrease in pulsatile modulation.

If there is no decrease, then similar to the previous embodiment, flow control can pass through to step S618 where the velocity vector field is determined from the acquired one or more angiographic images. It there however a decrease in pulsatile modulation is registered, flow control passes to a step S720 to lower the contrast agent rate. The previous steps are then repeated as in the precious embodiment until in step S715 it is determined that there was no decrease. In a simpler embodiment, the above loop is passed just once. If it is determined that a decrease in pulsatile modulation occurred, the power injector rate is lowered by a fixed amount and this reduced power injector rate is then maintained throughout the instant image run. In one embodiment the step S610 and S710 are combined and both, the flow rate and the pulsatilty index are computed and a combined upper threshold is formed, for example by taking the maximum or a weighted average of the two respective contrast agent injection rates.

The components of controller FC are shown as separate modules arranged in the controller FC itself. However, in one embodiment a distributed architecture and connected in a suitable communication network is also envisaged.

The controller FC and/or its components may be arranged as dedicated FPGAs or as hardwired standalone chips. In one embodiment, controller FC is resident on work station CON running as software routine. Controller FC and its components may be programmed in a suitable scientific computing platform such as Matlab® or Simulink® and then translated into C++ or C routines maintained in a library and linked when called on by work station CON. Controller FC may also be integrated in injector's PJ control logic or in the X-ray image 100. The user interface generator or controller UIC and/or the graphics display controller GDC may be included into the controller FC. However in other embodiments of controller FC, the controller UIC and/or controller GDC are external components of workstation CON and controller has suitably configured interface controllers and drivers to connect with controller UIC and/or controller GDC.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging system comprising:
   an imager for acquiring images of an object at a region of interest;
   a power injector for administering a contrast agent to a fluid of the object;
   a closed-loop feedback controller for controlling a contrast agent flow rate of the power injector and a radiation dosage of the imager, comprising:
   an input port for receiving i) a current power injector setting and ii) one or more current images of the object, the current one or more image acquired by the imager whilst the fluid is flowing or resides in the object's region of interest and acquired during or after administration into the fluid of the contrast agent by the power injector at a current contrast agent flow rate according to the current power injector setting;
   a fluid property determiner configured to determine, by using in-image information of the current one or more image, a physical property of the fluid comprising the administered contrast agent;
   a power injector setting determiner configured to,
      determine a desired contrast agent flow rate based on the determined physical property of the fluid comprising the administered contrast agent, wherein the desired contrast agent flow rate is a maximum threshold for the contrast agent flow rate of the power injector and wherein the maximum threshold is a percentage value between 30%-40% of the physical property of the fluid comprising the administered contrast agent, and
      determine whether the contrast agent flow rate is greater than the maximum threshold for the contrast agent flow rate; and
   an adjustment back-end configured to interface with
      the power injector for re-adjusting the power injector setting to effect the desired contrast agent flow rate, so as to reduce the contrast agent flow rate to less than or equal to the maximum threshold, and
      wherein the current one or more images or one or more follow-up images are displayed on a screen, the closed-loop feedback controller comprising a graphical user interface generator for generating on the screen a graphical user interface configured to allow a user to select in the current one or more images, when displayed, a sub-image, flow rate determiner, flow pattern determiner or image contrast determiner configured to determine in response to the user selected sub-image a current fluid flow rate by using in-image information only in the sub-image; and
   a logic module configured to,
      monitor an upper threshold and a lower threshold of the radiation dosage of the imager, and
      determine whether the upper threshold is lower than lower threshold, wherein when the upper threshold is lower than the lower threshold, the logic module resolves the inconsistency of the upper and lower threshold of the radiation dosage of the imager.

2. The system of claim 1, wherein the fluid property determiner is configured to determine, by using in-image information of the current one or more images, the current fluid flow rate of the fluid comprising the administered contrast agent.

3. The system of claim 2, wherein the current fluid flow rate is the physical property of the fluid comprising the administered contrast agent.

4. The system of claim 1, further comprising a fluid flow analyzer configured to determine a velocity field of the fluid comprising the administered contrast agent at the region of interest based on the one or more follow-up images acquired by the imager whilst the power injector administers contrast agent at the determined desired contrast agent flow rate.

5. The system of claim 1, further comprising
   an image contrast determiner configured to measure an image contrast in the current one or more image or in the one or more follow-up images, the adjustment back-end configured to interface with i) the power injector for re-adjusting the power injector setting to effect an increase of the contrast agent flow rate if the determined contrast is below a pre-defined contrast threshold or the adjustment back-end configured to interface with ii) the imager to adjust the radiation dosage.

6. The system of claim 1, wherein the fluid is pulsatile and wherein the fluid property determiner operates as a flow pattern determiner configured to measure pulsatile modulation across the current one or more image, said measurement based on contrast in the current one or more image, the adjustment back-end configured to interface with the power injector for re-adjusting the power injector setting to effect a decrease of the contrast agent flow rate if the measured contrast based pulsatile modulation is below a pre-defined pulsatility threshold.

7. The system of claim 1, wherein, initially, the power injector administers the contrast agent in a ramp-up phase wherein the contrast agent flow rate rises essentially linearly with pre-defined slope, wherein the closed-loop feedback controller operates during this ramp-up phase to determine the desired contrast agent flow.

8. The system of claim 4, comprising a graphics display controller configured to display on a screen a graphic depiction of the determined fluid velocity field as computed by fluid flow analyzer.

9. The system of claim 1 comprising the power injector for injecting the contrast agent before or after image acquisition by the imager.

10. A method of controlling a power injector, comprising:
   acquiring, by an imager, images of an object at a region of interest;
   administering, by a power injector, a contrast agent to a fluid of the object;
   receiving i) a current power injector setting and ii) a current one or more images of the object, the current one or more images acquired by the imager whilst the fluid is flowing or resides in the object's region of interest and acquired during or after administration into the fluid of the contrast agent by the power injector at a current contrast agent flow rate according to the current power injector setting;

determining, by using in-image information of the current one or more images, a physical property of the fluid comprising the administered contrast agent;

determining a desired contrast agent flow rate based on the determined physical property of the fluid comprising the administered contrast agent, wherein the desired contrast agent flow rate is a maximum threshold for the contrast agent flow rate of the power injector and wherein the maximum threshold is a percentage value between 30%-40% of the physical property of the fluid comprising the administered contrast agent;

determining whether the contrast agent flow rate is greater than the maximum threshold for the contrast agent flow rate; and adjusting the power injector setting to effect the desired contrast agent flow rate, so as to reduce the contrast agent flow rate to less than or equal to the maximum threshold, wherein the current one or more images or one or more follow-up images are displayed on a screen, a closed-loop feedback controller controlling a radiation dosage of the imager wherein an upper threshold and a lower threshold of the radiation dosage is monitored to determine whether the upper threshold is lower than lower threshold, wherein when the upper threshold is lower than the lower threshold, a logic module is used to resolve the inconsistency of the upper and lower threshold of the radiation dosage, comprises a graphical user interface generator for generating on the screen a graphical user interface configured to allow a user to select in the current one or more images, when displayed, a sub-image, flow rate determiner, flow pattern determiner or image contrast determiner configured to determine in response to the user selected sub-image a current fluid flow rate by using in-image information only in the sub-image.

11. The method of claim 10, wherein the step of determining the physical property of the fluid includes determining the current fluid flow rate of the fluid.

12. The method of claim 10 wherein the step of determining the physical property of the fluid includes determining an amount or degree of pulsatile modulation of the fluid including the contrast agent.

13. The method of claim 10 comprising:

determining a vector field of the fluid comprising the administered contrast agent at the region of interest based on one or more follow-up images acquired by the imager whilst the power injector administers contrast agent at the determined desired contrast agent flow rate; and displaying on a screen a graphic depiction of the determined vector field.

14. A non-transitory computer readable medium having stored thereon a computer program element comprising operations for controlling a power injector, the operations comprising:

acquiring, by an imager, images of an object at a region of interest;

administering, by a power injector, a contrast agent to a fluid of the object;

receiving i) a current power injector setting and ii) a current one or more images of an object, the current one or more images acquired by the imager whilst the fluid is flowing or resides in the object's region of interest and acquired during or after administration into the fluid of the contrast agent by the power injector at a current contrast agent flow rate according to the current power injector setting;

determining, by using in-image information of the current one or more images, a physical property of the fluid comprising the administered contrast agent;

determining a desired contrast agent flow rate based on the determined physical property of the fluid comprising the administered contrast agent, wherein the desired contrast agent flow rate is a maximum threshold for the contrast agent flow rate of the power injector and wherein the maximum threshold is a percentage value between 30%-40% of the physical property of the fluid comprising the administered contrast agent;

determining whether the contrast agent flow rate is greater than the maximum threshold for the contrast agent flow rate; and adjusting the power injector setting to effect the desired contrast agent flow rate, so as to reduce the contrast agent flow rate to less than or equal to the maximum threshold, wherein the current one or more images or one or more follow-up images are displayed on a screen, a closed-loop feedback controller controlling a radiation dosage of the imager wherein an upper threshold and a lower threshold of the radiation dosage is monitored to determine whether the upper threshold is lower than lower threshold, wherein when the upper threshold is lower than the lower threshold, a logic module is used to resolve the inconsistency of the upper and lower threshold of the radiation dosage, comprises a graphical user interface generator for generating on the screen a graphical user interface configured to allow a user to select in the current one or more images, when displayed, a sub-image, flow rate determiner, flow pattern determiner or image contrast determiner configured to determine in response to the user selected sub-image a current fluid flow rate by using in-image information only in the sub-image.

\* \* \* \* \*